US009308305B2

(12) United States Patent
Chen et al.

(10) Patent No.: US 9,308,305 B2
(45) Date of Patent: Apr. 12, 2016

(54) IMPLANTABLE BLOOD PUMP WITH INTEGRATED CONTROLLER

(71) Applicants: Keming Chen, Torrance, CA (US); Chen Chen, Santa Barbara, CA (US); Frank Lin, Torrance, CA (US)

(72) Inventors: Keming Chen, Torrance, CA (US); Chen Chen, Santa Barbara, CA (US); Frank Lin, Torrance, CA (US)

(73) Assignee: CH Biomedical (USA) Inc., Torrance, CA (US)

( * ) Notice: Subject to any disclaimer, the term of this patent is extended or adjusted under 35 U.S.C. 154(b) by 0 days.

(21) Appl. No.: 14/308,177

(22) Filed: Jun. 18, 2014

(65) Prior Publication Data

US 2015/0367049 A1 Dec. 24, 2015

(51) Int. Cl.
*A61N 1/362* (2006.01)
*A61M 1/12* (2006.01)
*A61M 1/10* (2006.01)

(52) U.S. Cl.
CPC ............. *A61M 1/122* (2014.02); *A61M 1/1086* (2013.01)

(58) Field of Classification Search
CPC ..... A61M 1/10; A61M 1/1015; A61M 1/101; A61M 1/122; A61M 1/1086
IPC .................... A61M 1/10, 1/1015, 1/101, 1/122, A61M 1/1086
See application file for complete search history.

(56) References Cited

U.S. PATENT DOCUMENTS

| 6,066,086 A | 5/2000 | Antaki et al. |
| 6,149,683 A | 11/2000 | Lancisi et al. |
| 6,183,412 B1 * | 2/2001 | Benkowski et al. ............ 600/16 |
| 6,394,769 B1 | 5/2002 | Bearnson et al. |
| 8,597,350 B2 | 12/2013 | Rudser et al. |
| 2013/0245614 A1 | 9/2013 | Seebruch |
| 2014/0039241 A1 | 2/2014 | Jarvik |
| 2014/0066691 A1 | 3/2014 | Siebenhaar |
| 2014/0288352 A1 | 9/2014 | Yanai et al. |
| 2014/0303426 A1 | 10/2014 | Kerkhoffs et al. |

FOREIGN PATENT DOCUMENTS

WO WO2011081626 A1 7/2011

OTHER PUBLICATIONS

International Search Report and Written Opinion of the International Searching Authority, dated Sep. 23, 2015.

* cited by examiner

*Primary Examiner* — George Manuel
(74) *Attorney, Agent, or Firm* — Seyfarth Shaw LLP

(57) ABSTRACT

An implantable blood pump includes motor control circuitry and power electronics circuitry integrated within the implantable pump body. The motor control circuitry and power electronics circuitry is configured to energize and control motor windings to rotate the pump rotor and impeller. Additional control circuitry and power electronics circuitry may be integrated within the pump housing to energize and control magnetic bearings of a magnetic levitation pump. A percutaneous cable coupled between the implantable blood pump and an extracorporeal monitor includes a reduced number of leads to provide power and control signals to the implantable blood pump. Wireless communication between the extracorporeal monitor and the integrated power electronics and control circuitry facilitates the use of a percutaneous cable with as few as two leads for providing power to the implantable pump.

20 Claims, 9 Drawing Sheets

IMPLANTABLE BLOOD PUMP WITH INTEGRATED CONTROLLER

FIELD OF TECHNOLOGY

The present disclosure relates to implantable ventricular assist devices (VADs) and more particularly to integrated control and power circuitry in a VAD.

BACKGROUND

Ventricular assist devices (VADs) include blood pumps, which are used to help patients who suffer from poor blood circulation and heart disease. VAD can be implanted in the patient's body to assist the heart and provide improved blood circulation. An implanted VAD may be powered by an electrical power source located outside of the patient's body. Power is transmitted from the electrical power source to the implanted VAD via percutaneous cable.

An implanted VAD is powered and controlled by electronic components. It is also desirable to place such electronic components inside the human body so that the temperature shift can be significantly reduced. Also, placing such electronic components inside the human body facilitates a reduced number of leads inside the cable. This reduces the size of the cable and helps to improve reliability of the system when the cable is subject to wear, fatigue and other damages due to mistaken handling of the cable by patients. A further advantage to reduce the number of leads in the cable is to improve electromagnetic compatibility since the cable is exposed to electromagnetic interference from the environment, but electronics inside the human body does not.

A conventional blood pump in a VAD is driven by one or more three-phase electric motors such as a brushless direct current (DC) three-phase motor or an alternating current (AC) type three-phase motor. The motor's windings receive electric currents from power electronics. In conventional practice, the power electronics are configured outside of the blood pump, so at least three leads (wires), which correspond to the three phases of the pump motor, are used in the percutaneous cable to connect the power electronics outside of the pump and the motor windings inside the pump.

Some conventional VADs include a pump rotor configuration which employs magnetic suspension (i.e., magnetic bearings) for the rotor. A magnetic suspension system is used to stabilize one or more degrees of freedom of the rotor. For each degree of freedom, a feedback loop incorporates a sensor, which detects the position of the rotor, a controller, which receives signal from the sensor and then generates a control signal through sophisticated signal processing, and a power electronics unit, which generates electric current following the command of the control signal. The electric current then flows into the windings in the magnetic bearing to create magnetic force on the rotor.

Conventionally, both the controller and the power electronics are placed outside of the blood pump. Additional leads within percutaneous cable are used to feed the position sensor signal from inside the pump to the controller outside of the pump. Additional leads within percutaneous cable are used to connect the power electronics outside of the pump to the magnetic bearing windings inside the pump. That means at least four leads are required if one degree of freedom of the rotor is stabilized by the magnetic bearing. More leads are required if more than one degree of freedom are actively controlled by magnetic bearings.

The use of a VAD involves subjecting a patient to certain risks including the risk of infection at the site where the percutaneous cable penetrates the skin. To reduce the risk of infection, it is desirable to have percutaneous cable as small and flexible as possible. Therefore, it is desirable to reduce the number of leads inside the percutaneous cable.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

Figure 1:
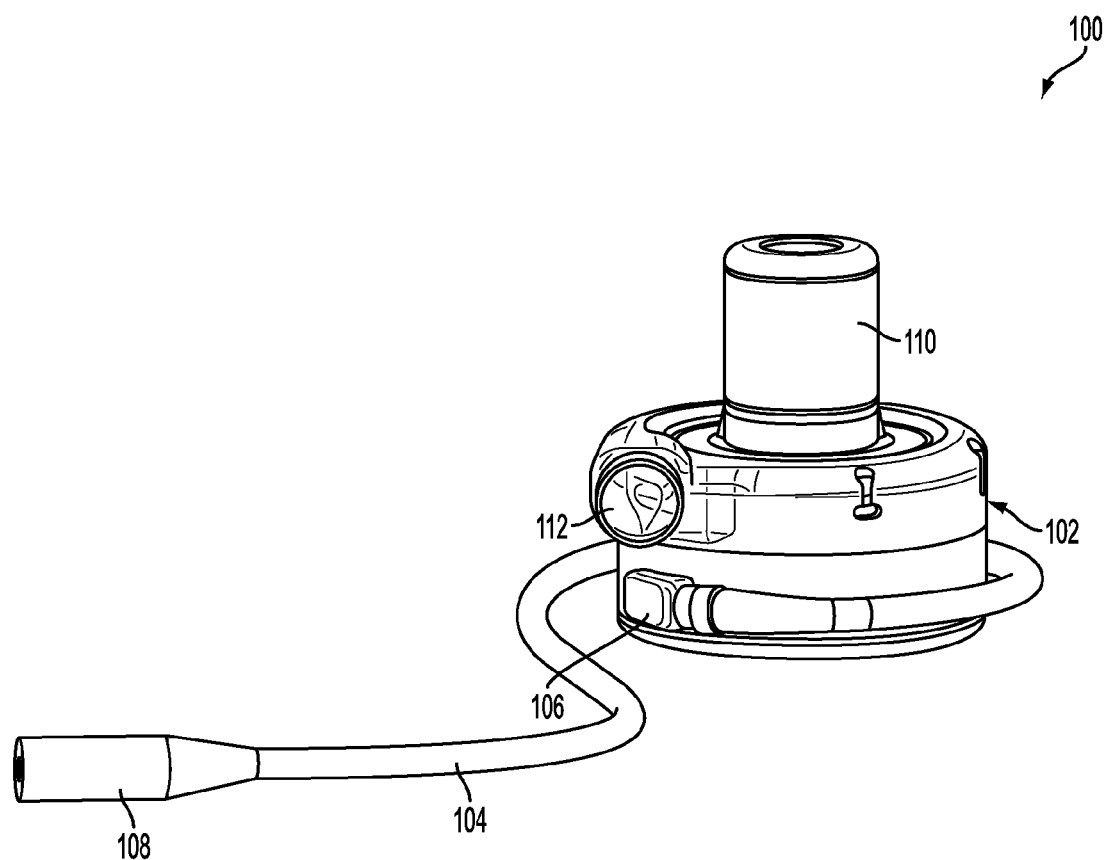
FIG. 1 is an illustration of an implantable blood pump with a percutaneous cable according to an aspect of the present disclosure.

It should be understood that the comments included in the notes as well as the materials, dimensions and tolerances discussed therein are simply proposals such that one skilled in the art would be able to modify the proposals within the scope of the present disclosure.

DETAILED DESCRIPTION OF THE INVENTION

While aspects of the present disclosure include embodiments in many different forms, there is shown in the drawings, and will herein be described in detail, a preferred embodiment of the disclosure with the understanding that the present application is to be considered as an exemplification of the principles of the disclosure and is not intended to limit the broad aspect of the disclosure to embodiments illustrated.

The following detailed description is of the best currently contemplated modes of carrying out exemplary embodiments of the disclosure. The description is not to be taken in a limiting sense, but is made merely for the purpose of illustrating the general principles of the disclosure, since the scope of the disclosure is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

According to aspects of the present disclosure, a small pump for a ventricular assist device (VAD) includes integrated power electronics and controller circuitry. The disclosed VAD pump with integrated power electronics and controller circuitry can be implanted completely in the pericardial space directly adjacent to the heart of a patient.

Referring to FIG. 1, a VAD according to an aspect of the present disclosure includes an implantable pump apparatus 100 in which power electronics and control circuitry for the pump are incorporated within a common pump body 102. The pump body 102 encloses the pump's impeller and motor including the motor's rotor and magnetic bearings along with the power electronics and control circuitry for driving and controlling the motor and magnetic bearings.

The implantable pump apparatus 100 transports blood from an inlet 110 to an outlet 112. A proximal end of a percutaneous cable 104 extends into the pump body 102 at a feedthrough 106 to deliver power and control signals for the operation of the pump. A distal end of the percutaneous cable 104 includes an extracorporeal monitor connector 108, for connecting to an extracorporeal monitor (see FIG. 3). The feedthrough 106 prevents leakage of liquid or air into the pump while permitting electric current flowing into the pump apparatus 100.

Figure 2:
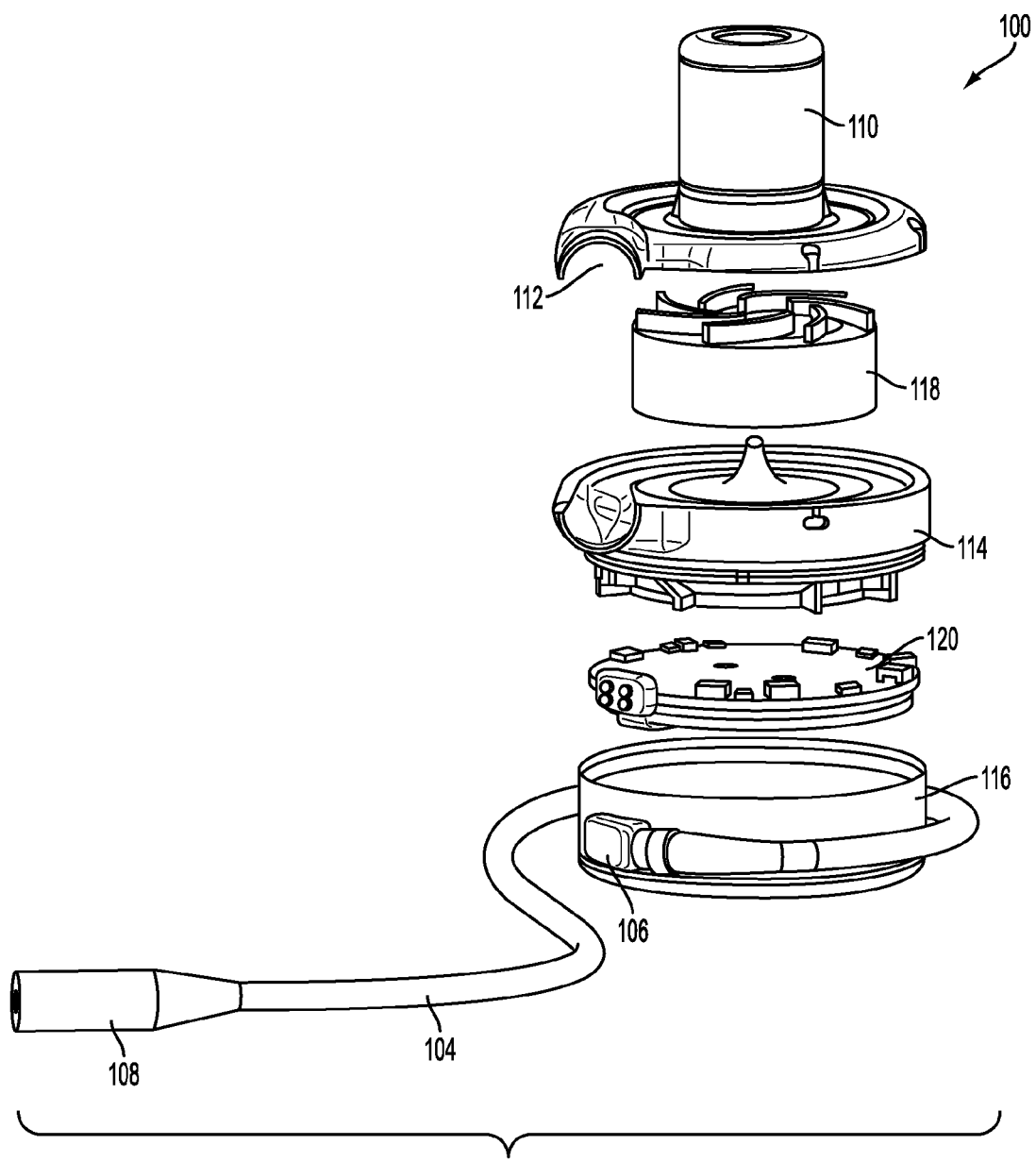
FIG. 2 is an illustration of an implantable pump with a percutaneous cable and integrated power electronics and controller components according to an aspect of the present disclosure.

Referring to FIG. 2, according to an aspect of the present disclosure, the pump apparatus 100 includes a rotor and impeller assembly 118 configured in a pump housing 114. The pump housing 114, locates the pump motor and forms an intermediate portion of the pump body 102. A top portion of the pump body 102 including the pump inlet 110 is coupled to the pump housing. A bottom portion of the pump body 102 includes a casing 116, which is coupled to the pump housing 114 opposite the pump inlet 110. The rotor and impeller assembly 118 includes a rotor coupled to an impeller. The rotor is driven by an electric motor stator (not shown) inside the pump housing 114. The rotor may be suspended with mechanical bearings, hydrodynamic bearings, or magnetic bearings. In implementations that include magnetic bearings, magnetically actuating components (not shown) are installed inside the pump housing 114. Such actuating components are similar to an electric motor stator in that they comprise electric windings wound on magnetic poles made of magnetic materials. Electric current in these windings creates magnetic fields and consequently induces magnetic force exerted on the rotor. By actively controlling the direction and magnitude of the current, the magnetic forces on the rotor is continuously adjusted so that the rotor is stabilized in the magnetic field. The active control is provided by a feedback control system that includes power electronics and control circuits. In a conventional arrangement, the power electronics and controllers for both motor and magnetic bearings are bulky and had to be placed outside of the pump, usually installed in the extracorporeal monitor (see FIG. 3). According to aspects of the present disclosure, by making use of the advanced technology of miniaturized IC chips, the power electronics and controller are made small enough to be installed inside the implantable blood pump.

According to an aspect of the present disclosure an electronics module 120, such as a printed circuit board, for example, is enclosed within the bottom portion of the pump body 102 between the pump housing 114 and the casing 116. The electronics module includes power circuitry and control circuitry configured for operating the pump motor and magnetic bearings and is coupled to the percutaneous cable 104.

A VAD according to an aspect of the present disclosure is described with reference to FIG. 3. According to this aspect of the disclosure, the rotor and impeller assembly 118 is magnetically suspended and is rotationally driven by an electric motor, including the rotor and motor windings 132. The motor may be a three phase brushless dc motor or a three phase ac motor, for example. Power electronics and control circuitry 140 for the motor is built on the electronics module 120. In the illustrated embodiment, the motor control circuitry 140 inside the pump may include a microcontroller or a Digital Signal Processor. The motor control circuitry 140 uses a sensorless control scheme to drive the motor winding 132 with a pulse width modulated (PWM) signal which turns the rotor/impeller assembly 118.

Magnetic bearings stabilize one or more degrees of freedom of the rotor through active control. For each degree of freedom under control, one or more sensors, 136 such as eddy current displacement sensors, detect the position of the rotor. Magnetic levitation (maglev) control circuitry 142 receives and processes the sensor signal to generate a command signal that is applied to maglev power electronics. This signal controls the power electronics to direct electric current into the windings 134 of the magnetic bearings. The power electronics and controller for the magnetic bearings are also built on the electronic module 120. In the illustrated embodiment, the maglev control circuitry 142 includes an analog to digital (A/D) converter which receives analog position signals from the magnetic bearing (maglev) sensors 136 and converts them to digital signals. The digital signals are then used to create a PWM signal to drive the maglev windings 134 which provide active magnetic bearing control to suspend the rotor. Besides, other control strategies for the feedback control of a magnetic bearing, commonly used by people skilled in the art, may be applied.

The power electronics and controller module 120 receives power and certain control commands from an extracorporeal monitor 122. The extracorporeal monitor 122 includes power management circuitry 124, which receives power from a power source 128. The power source 128 may include rechargeable batteries, alternating current or other types of power source. The power management circuitry 124 supplies power into the power electronics and controller module 120 inside the pump body. Since the entire functions of the motor and magnetic bearing control are performed in the power electronics and controller module 120, the power management circuitry 124 does not need to serve any more function except for supplying power to the electronic module 120. Therefore, in this implementation, only one pair of leads in the percutaneous cable 104 is used to serve as power line.

The extracorporeal monitor 122 also includes communication circuitry 126, which exchanges information with the motor controller and/or the magnetic bearing controller in the electronic module 120 inside the pump. The communication circuitry 126 provides top-level commands to set the operating conditions of the motor and/or the magnetic bearings, such as setting and altering the pump speed. It also serves diagnostic functions based on received operating conditions such as pump speed and electric current of motor and of magnetic bearings, for example. In addition, it may be used to load program codes into the motor controller and/or the magnetic bearing controller in the electronic module 120. All such functions of the communication circuitry 126 can be fulfilled by using a microprocessor in combination with certain peripheral electronic circuits. Therefore, it is adequate to implement serial communication for connection between the communication circuitry 126 and the electronics module 120, which requires merely 2 leads in the percutaneous cable 104. Therefore, according to an aspect of the disclosure this implementation is operative using only four leads 125 inside the percutaneous cable, one pair of power line and the other pair of serial communication.

Figure 3:
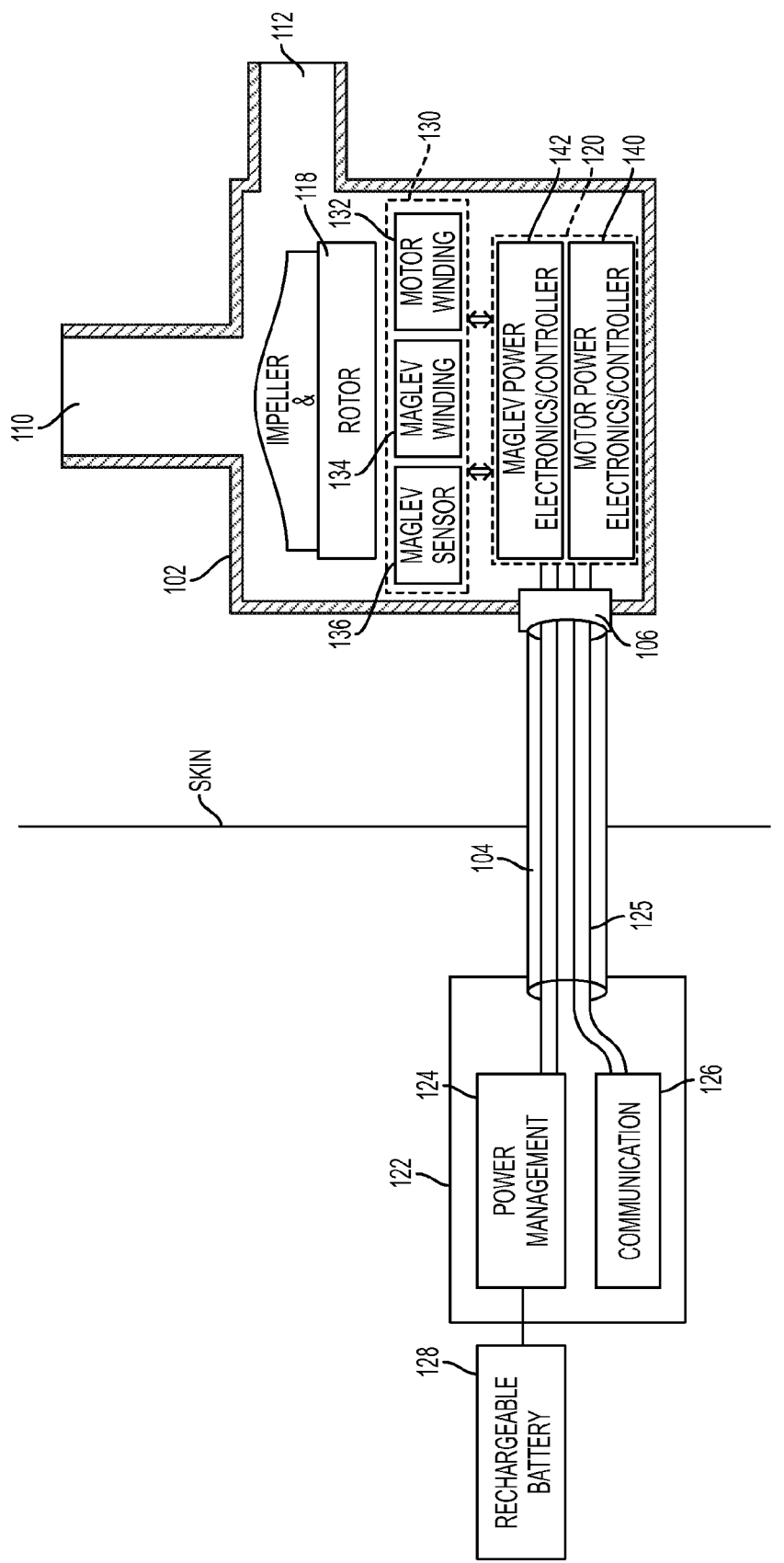
FIG. 3 is a graphical block diagram of an implantable magnetically suspended blood pump with integrated power electronics and controller implemented with only four leads inside a percutaneous cable according to an aspect of the present disclosure.
Figure 4:
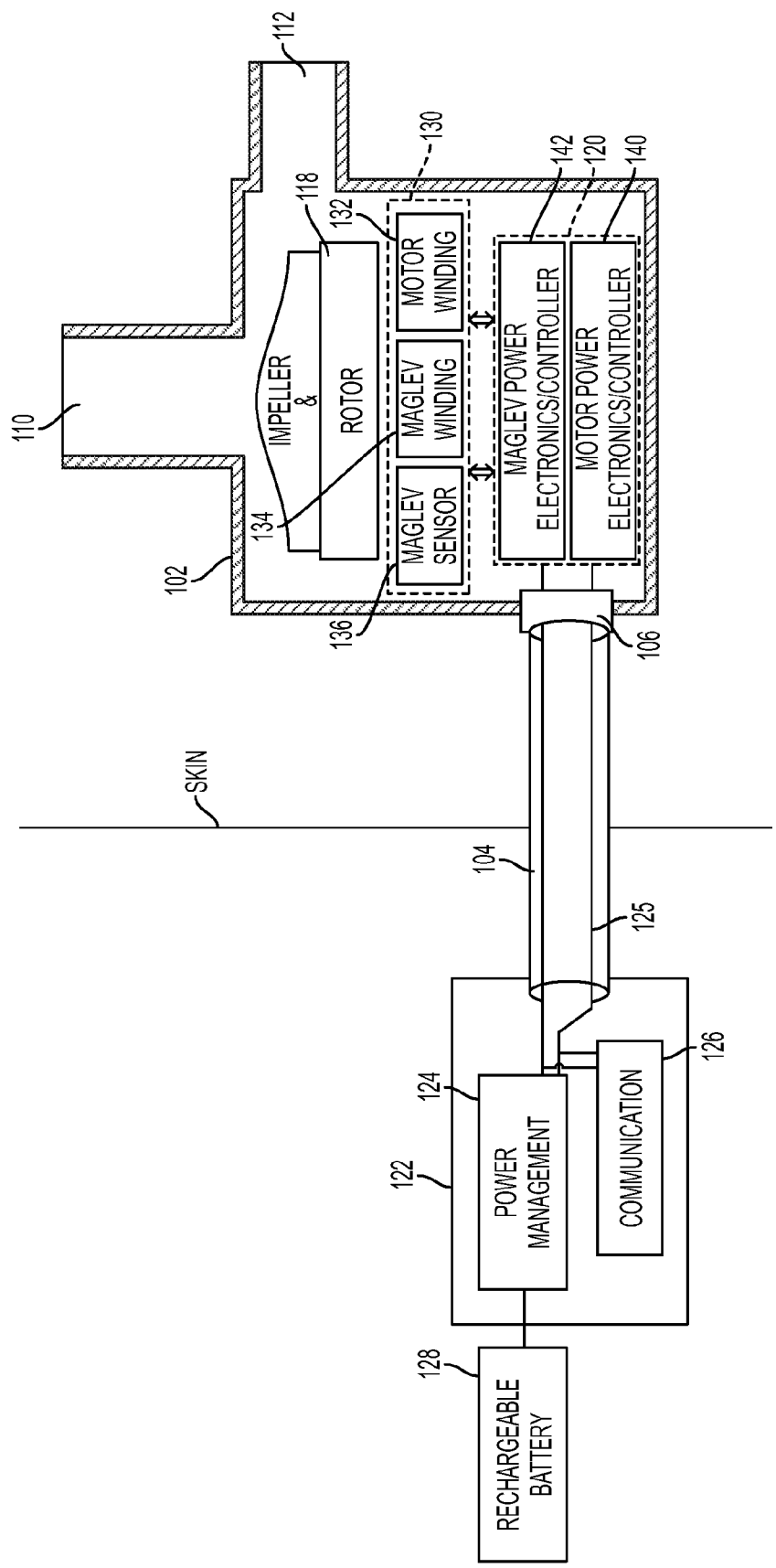
FIG. 4 is a graphical block diagram of an implantable magnetically suspended blood pump with integrated power electronics and controller implemented with only two leads inside the percutaneous cable according to an aspect of the present disclosure.

FIG. 4 illustrate a variation of the embodiment in FIG. 3 in which communication signals between the communication circuitry 126 in the extracorporeal monitor 122 and the power electronics/controller module 120 inside the pump are modulated by a high frequency carrier signal and superimposed onto power leads 125 in the percutaneous cable 104. A modulation and a demodulation circuit may be connected between the extracorporeal monitor 122 and the power electronics/controller module 120 inside the pump to provide the needed communication. According to an aspect of the disclosure this implementation is operative using only two leads inside the percutaneous cable to carry both power and communication signals.

Figure 5:
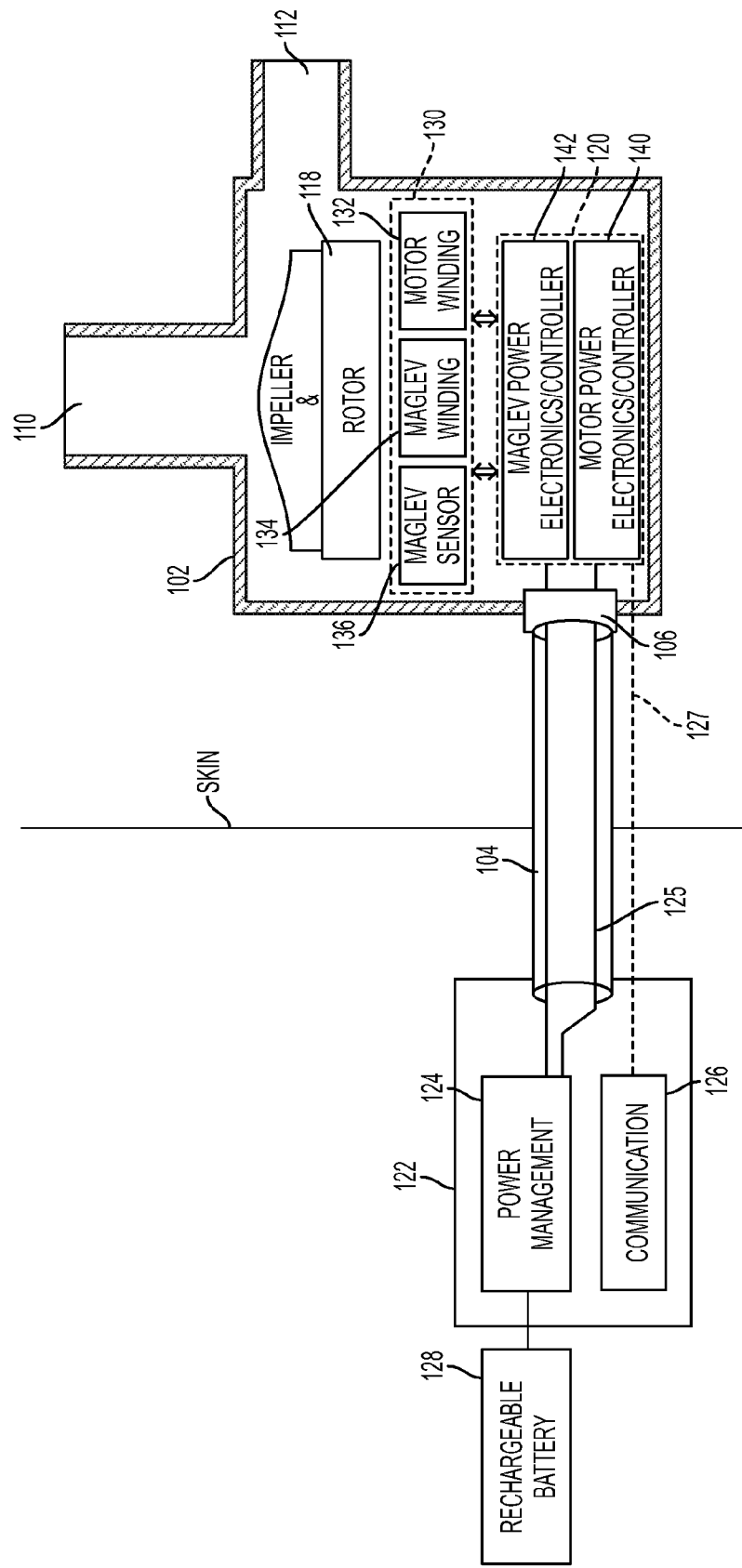
FIG. 5 is a graphical block diagram of an implantable magnetically suspended blood pump with integrated power electronics and controller implemented with two leads inside the percutaneous cable in combination with wireless communication between the external monitor and the integrated controllers according to an aspect of the present disclosure.

FIG. 5 illustrates one embodiment of the present disclosure which is similar to the embodiment illustrated in FIG. 4 except that the communication circuitry 126 in the extracorporeal monitor 122 is configured to communicate with the power electronics/controller module 120 inside the pump through a wireless connection 127. According to an aspect of the disclosure this implementation is operative using only two leads 125 inside the percutaneous cable for providing power supply.

Figure 6:
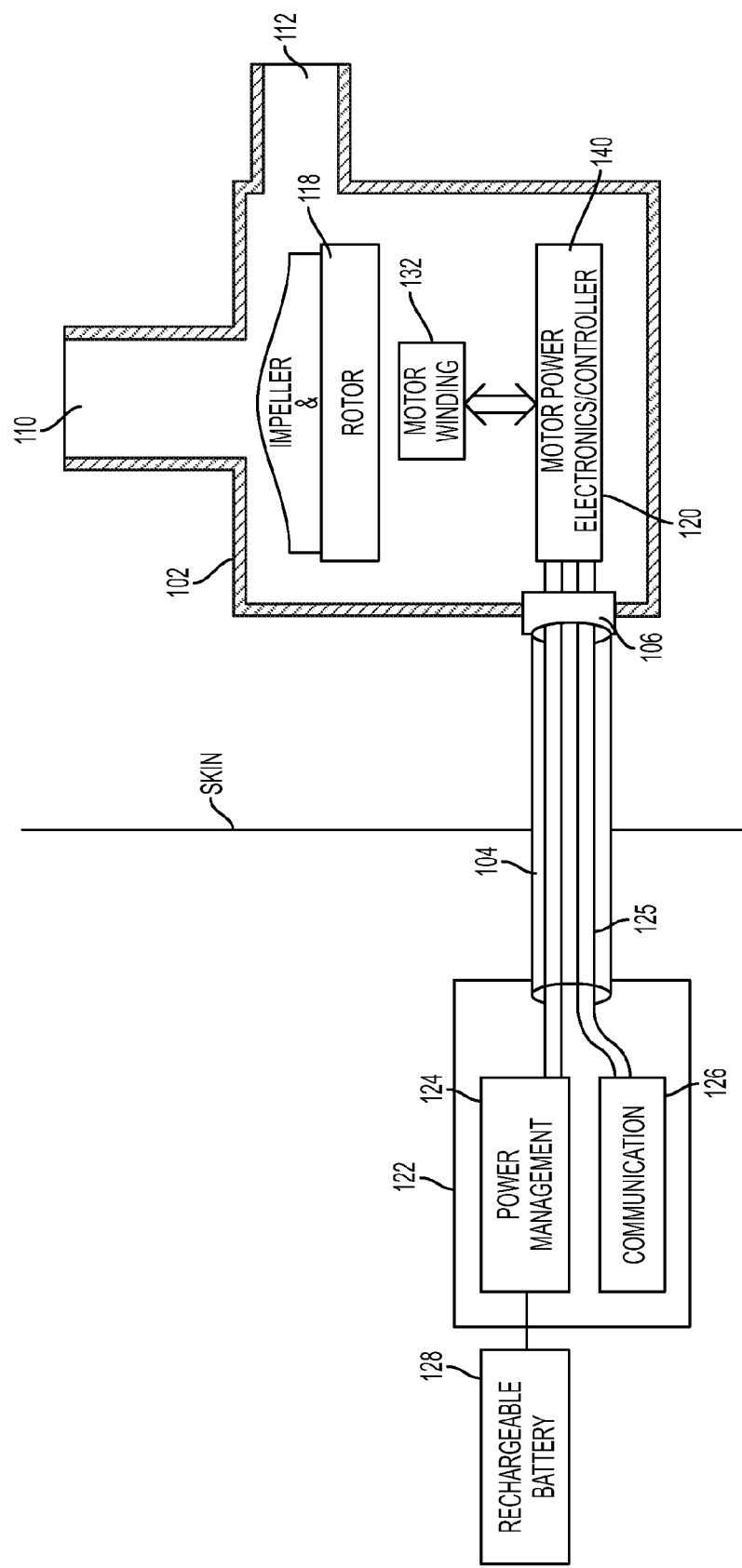
FIG. 6 is a graphical block diagram of an implantable blood pump with integrated power electronics and controller for the motor implemented with only four leads inside the percutaneous cable according to an aspect of the present disclosure.

According to another aspect of the present disclosure, FIG. 6 illustrates an implantable blood pump, which is different from the pump illustrated in FIGS. 3-5. In the implementation shown in FIG. 6, the pump rotor is suspended with other means than magnetic bearing, and thus no magnetic bearing electronics is included. The pump is still rotationally driven by an electric motor. Therefore, the power electronics/controller module 120 contains merely power electronics and control circuitry 140 for the motor. According to an aspect of the disclosure this implementation is operative using only four leads 125 inside the percutaneous cable in which two leads provide communication signals and two leads serve power line.

Figure 7:
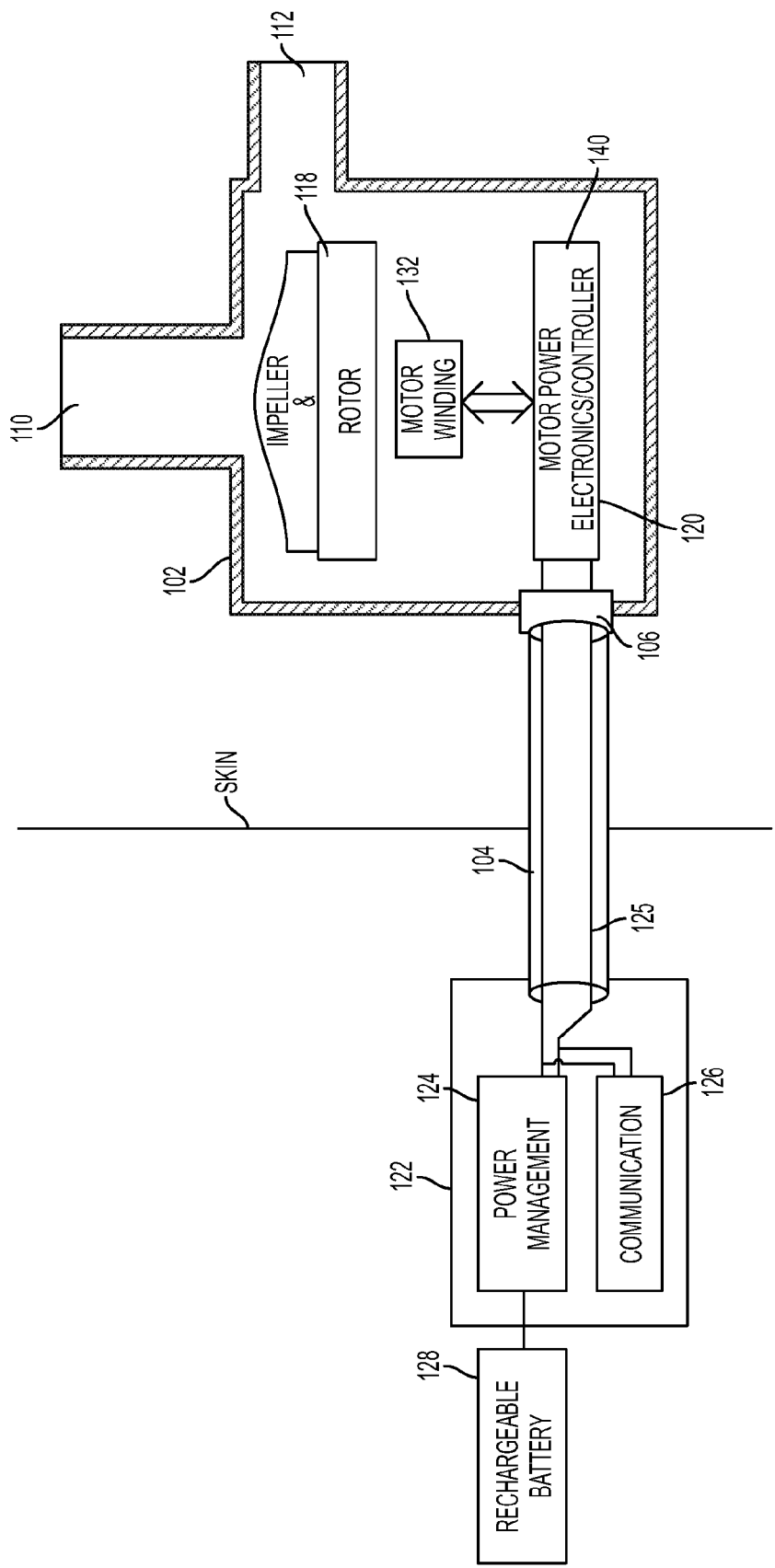
FIG. 7 is a graphical block diagram of an implantable blood pump with integrated power electronics and controller for the motor implemented with two leads inside the percutaneous cable according to an aspect of the present disclosure.

According to an aspect of the present disclosure FIG. 7 illustrates an implantable blood pump that does not have magnetic bearing. In this implementation, communication signals between the communication circuitry 126 in the extracorporeal monitor 122 and the power electronics/controller module 120 inside the pump are modulated by a high frequency carrier signal and superimposed onto power leads 125 in the percutaneous cable 104. A modulation and a demodulation circuit may be connected between the extracorporeal monitor 122 and the power electronics/controller module 120 inside the pump to provide the needed communication. According to an aspect of the disclosure this implementation is operative using only two leads inside the percutaneous cable to carry both power and communication signals.

Figure 8:
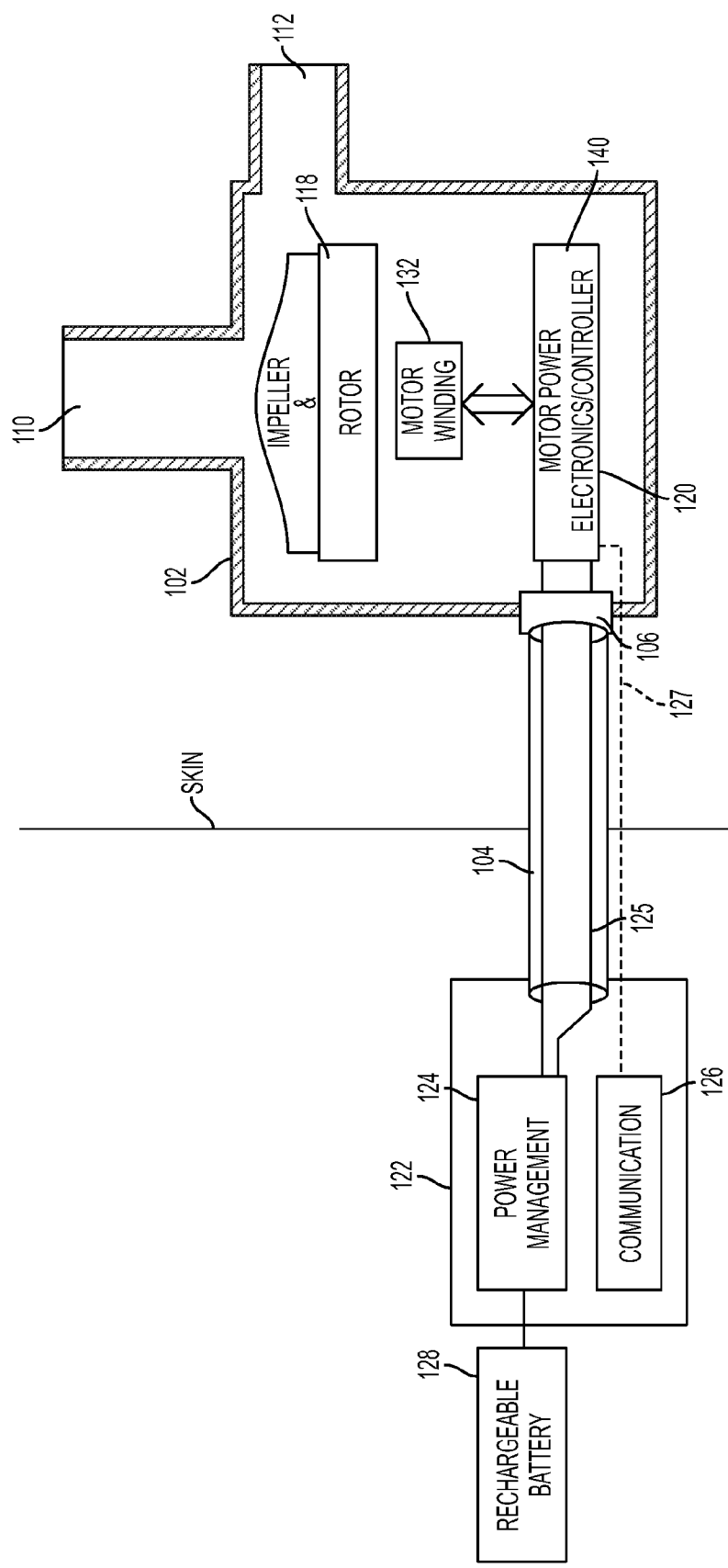
FIG. 8 is a graphical block diagram of an implantable blood pump with integrated power electronics and controller for the motor implemented with only two leads inside the percutaneous cable in combination with wireless communication between the external monitor and the integrated controllers according to an aspect of the present disclosure.

According to an aspect of the present disclosure FIG. 8 illustrates an implantable blood pump that does not have magnetic bearing. This embodiment is similar to the embodiment illustrated in FIG. 5 in which a wireless connection 127 is used for communication between the external monitor 122 and the power electronics and control module 120 inside the pump. The percutaneous cable has only two leads providing power from extracorporeal monitor to the integrated motor controller inside the pump. According to an aspect of the disclosure this implementation is operative using only two leads inside the percutaneous cable for providing power supply.

Figure 9:
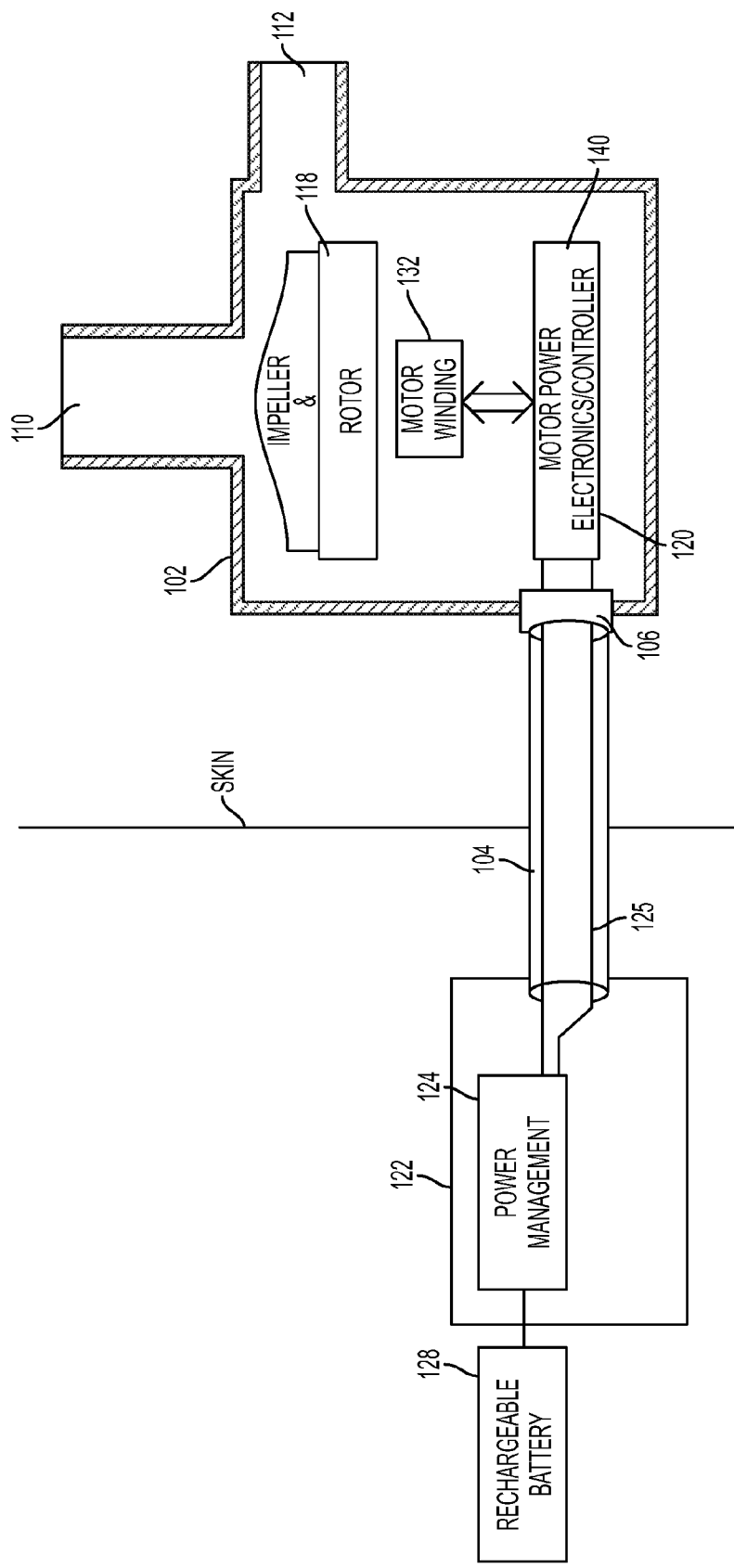
FIG. 9 is a graphical block diagram of an implantable blood pump with integrated power electronics for the motor that implemented with two leads inside the percutaneous cable according to an aspect of the present disclosure.

FIG. 9 illustrates another embodiment according to an aspect of the present disclosure in which pump motor does not need communication with the outside of the pump. The motor power electronics and control circuitry 140 receives power from the power management module 124 in the extracorporeal monitor 122 through the power line 125 in the percutaneous cable. It uses the power to produce commutated three-phase current into the motor windings 132 and drives the rotor and impeller assembly 118. No commands or other information from outside is required for the motor to operate in such way. Accordingly, in this embodiment no communication circuitry is needed in the extracorporeal monitor 122. According to an aspect of the disclosure this implementation is operative using only two leads 125 inside the percutaneous cable for providing power signals.

As used herein, the term "coupled" or "communicably coupled" can mean any physical, electrical, magnetic, or other connection, either direct or indirect, between two parties. The term "coupled" is not limited to a fixed direct coupling between two entities. The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

The invention claimed is:

1. An implantable pump apparatus comprising:
an implantable pump body enclosing a pump motor, rotor, impeller, and motor windings;
a power and controller module enclosed within the pump body and including:
first power electronics circuitry coupled to the motor windings for operating the pump motor; and
first control circuitry adapted to control the pump motor; and
a percutaneous cable coupled to the power and controller module, the percutaneous cable including two shared leads adapted to provide power to the implantable pump apparatus and exchange information and/or control signals between the power and controller module and an extracorporeal monitor.

2. The apparatus of claim 1, wherein the percutaneous cable does not include additional leads other than the two shared leads.

3. The apparatus of claim 1, wherein the extracorporeal monitor is adapted to superimpose a high frequency carrier signal onto a power signal on the shared leads, the high frequency carrier signal modulated to include control information.

4. The apparatus of claim 1 wherein the motor comprises a three-phase electric motor.

5. The apparatus of claim 1, further comprising:
a magnetic bearing in the pump body, wherein the power and controller module includes:
second power electronics circuitry configured to power the magnetic bearing; and
second control circuitry adapted to control the magnetic bearing.

6. The apparatus of claim 5, wherein the percutaneous cable comprises only the two shared leads to provide power to the implantable pump apparatus for driving the motor and/or the magnetic bearings.

7. The apparatus of claim 5, wherein the percutaneous cable does not include additional leads other than the two shared leads.

8. The apparatus of claim 5, wherein the extracorporeal monitor is adapted to superimpose a high frequency carrier signal onto a power signal on the shared leads, the high frequency carrier signal modulated to include control information.

9. An implantable pump apparatus comprising:
an implantable pump body enclosing a pump motor, rotor, impeller, and motor windings;
a power and controller module enclosed within the pump body and including:
first power electronics circuitry coupled to the motor windings for operating the pump motor;
first control circuitry adapted to control the pump motor; and
first wireless communication circuitry in the implantable pump body adapted for wireless communication with second wireless communication circuitry in an extracorporeal monitor; and
a percutaneous cable coupled to the power and controller module, the percutaneous cable including two power leads adapted to provide power to the implantable pump apparatus.

10. The apparatus of claim 9, wherein the percutaneous cable does not include additional leads other than the two shared leads.

11. The apparatus of claim 9, further comprising:
a magnetic bearing in the pump body, wherein the power and controller module includes:
second power electronics circuitry enclosed within the pump body and adapted to power the magnetic bearing, and
second control circuitry adapted to control the magnetic bearing.

12. The apparatus of claim 11, wherein the percutaneous cable does not include additional leads other than the two power leads.

13. An implantable pump apparatus comprising:
an implantable pump body enclosing a pump motor, rotor, impeller, and motor windings;
a power and controller module enclosed within the pump body and including:
first power electronics circuitry coupled to the motor windings for operating the pump motor; and
first control circuitry adapted to control the pump motor; and
a percutaneous cable coupled to the power and controller module, the percutaneous cable including two power leads adapted to provide power to the implantable pump apparatus and
a signal lead adapted to exchange information and/or control signals between the power and controller module and an extracorporeal monitor.

14. The apparatus of claim 13, wherein the percutaneous cable includes only the two power leads, the signal lead and no other leads.

15. The apparatus of claim 13, further comprising:
a magnetic bearing in the pump body, wherein the power and controller module includes:
second power electronics circuitry enclosed within the pump body and adapted to power the magnetic bearing, and
second control circuitry adapted to control the magnetic bearing.

16. The apparatus of claim 15, wherein the percutaneous cable includes only the two power leads, the signal lead and no other leads.

17. An implantable pump apparatus comprising:
an implantable pump body enclosing a pump motor, rotor, impeller, motor windings, and a magnetic bearing;
a power and controller module enclosed within the pump body and including:
first power electronics circuitry coupled to the motor windings for operating the pump motor;
second power electronics circuitry adapted to power the magnetic bearing;
first and second control circuitry respectively adapted to control the pump motor and magnetic bearing; and
a percutaneous cable coupled to the power and controller module, the percutaneous cable including a signal lead adapted to exchange information and/or control signals between the outside and inside of the implantable pump body.

18. An implantable pump apparatus comprising:
an implantable pump body enclosing a pump motor, rotor, impeller, and motor windings;
a power and controller module enclosed within the pump body and including first power electronics circuitry coupled to the motor windings for operating the pump motor;
a percutaneous cable coupled to the power and controller module;
an extracorporeal monitor coupled to the percutaneous cable; and
a power source coupled to the extracorporeal monitor.

19. The apparatus of claim 18, wherein the extracorporeal monitor comprises:
a power management module; and
a communication module.

20. The apparatus of claim 19, further comprising first wireless communication circuitry disposed in the implantable pump body adapted for wireless communication with second wireless communication circuitry in the extracorporeal monitor.

* * * * *